United States Patent
El-Hay et al.

(10) Patent No.: US 9,189,764 B2
(45) Date of Patent: Nov. 17, 2015

(54) USAGE OF QUANTITATIVE INFORMATION GAIN TO SUPPORT DECISIONS IN SEQUENTIAL CLINICAL RISK ASSESSMENT EXAMINATIONS

(71) Applicant: International Business Machines Corporation, Armonk, NY (US)

(72) Inventors: Tal El-Hay, Modi'in (IL); Michal Flato, Tel Aviv (IL); Naama Parush-Shear-Yashuv, Neve-Daniel (IL)

(73) Assignee: International Business Machines Corporation, Armonk, NY (US)

(*) Notice: Subject to any disclaimer, the term of this patent is extended or adjusted under 35 U.S.C. 154(b) by 142 days.

(21) Appl. No.: 13/759,079

(22) Filed: Feb. 5, 2013

(65) Prior Publication Data
US 2014/0220539 A1 Aug. 7, 2014

(51) Int. Cl.
*G06F 17/00* (2006.01)
*G06Q 10/06* (2012.01)
*G06Q 50/22* (2012.01)
*G09B 7/08* (2006.01)

(52) U.S. Cl.
CPC ............ *G06Q 10/0635* (2013.01); *G06Q 50/22* (2013.01); *G09B 7/08* (2013.01)

(58) Field of Classification Search
CPC ......... G06Q 50/22; G06Q 50/24; G06F 19/32
USPC ...................................................... 706/12, 45
See application file for complete search history.

(56) References Cited

U.S. PATENT DOCUMENTS

| 7,209,835 | B1 | 4/2007 | Pearlman |
| 7,461,048 | B2* | 12/2008 | Teverovskiy et al. ........... 706/62 |
| 2009/0094063 | A1 | 4/2009 | Ennett |
| 2009/0202964 | A1* | 8/2009 | Simon .............................. 434/62 |
| 2011/0112380 | A1* | 5/2011 | Robinson ....................... 600/300 |

OTHER PUBLICATIONS

Snyder-Ramos, Stephanie A., et al. "Patient satisfaction and information gain after the preanesthetic visit: a comparison of face-to-face interview, brochure, and video.", 2005, Anesthesia & Analgesia 100.6 (2005): 1753-1758.*

Sharit, J., Czaja, S. J., Augenstein, J. S., Balasubramanian, G., & Schell, V. (2006). Assessing the information environment in intensive care units. Behaviour & Information Technology, 25(03), pp: 1-15.*

* cited by examiner

*Primary Examiner* — David Vincent
(74) *Attorney, Agent, or Firm* — Ziv Glazberg, Esq.

(57) ABSTRACT

A computer-implemented method and apparatus for supporting decisions in sequential clinical risk assessment examinations, the method comprising receiving one or more first test results and a question, both associated with a patient; and assessing by a processor associated with a computing platform, information gain provided by a second test which may be performed for the patient, as the conditional mutual information between a second test and the question, using the first test result.

15 Claims, 2 Drawing Sheets

USAGE OF QUANTITATIVE INFORMATION GAIN TO SUPPORT DECISIONS IN SEQUENTIAL CLINICAL RISK ASSESSMENT EXAMINATIONS

TECHNICAL FIELD

The present disclosure relates to clinical decision support systems in general, and to the usage of quantitative information measures to support decisions for further treatments or examinations, in particular.

BACKGROUND

A Clinical Decision Support System (CDSS or CDS) is a decision support system (DSS), which is designed to assist physicians and other health professionals with decision-making tasks, such as assigning tests or treatment for a patient. A clinical decision support system may be looked at as a knowledge system, which uses items of personal or medical data to provide medical case-specific advice.

CDSS may be used to assist clinicians at the point of care to decide whether and which examination or treatment to assign to their patient to help improve patient's care or diagnostic, while assessing the risks associated with the patient or with the system as a whole.

Predictive risk assessment models may use information driven from clinical tests, lifestyle and other personal and medical history details to predict a patient's future condition.

Current risk assessment models require a predetermined set of test results also referred to as biomarkers in order to perform. However there are cases where a subset of the biomarkers could provide the prediction with similar degree of confidence as the full model, thus making the additional tests redundant. Thus, models that require all biomarkers might in practice be performing unnecessary expensive, unpleasant or risky examinations, for example radiology scans or invasive pregnancy screening tests.

Some current models that can perform without all biomarkers may assume that values for the missing tests are randomly missing, or that the probability of the values being absent is known a-priori at the time of model generation.

Another set of models that can possibly perform without all biomarkers relates to decision trees. An examination can be avoided if a path from the root to the matching leaf does not involve the biomarkers corresponding to the examination. However, even if such a path exists, which may not be the case for all possible subsets, it is predefined at the model training time and cannot be dynamically adjusted at evaluation time to accommodate clinical state, personal preferences, financial limitations, resource availability, or other factors.

In view of the above, there is required a CDSS that may overcome the deficiencies of existing systems.

BRIEF SUMMARY

One aspect of the disclosure relates to a computer-implemented method performed by a computerized device, comprising: receiving one or more first test results and a question, both associated with a patient; and assessing by a processor associated with a computing platform, information gain provided by a second test which may be performed for the patient, as the conditional mutual information between a second test and the question, using the first test results.

Another aspect of the disclosure relates to a computer-implemented method performed by a computerized device, comprising: receiving a first test result and a question, both associated with a patient; assessing the information gain provided by a second test to be performed for the patient as the conditional mutual information between a second test and the question, using the first test result, in accordance with the formula of:

$$cInfoGain(Y, A_{n+1} | A_1 = a_1, \ldots, A_n = a_n) =$$

$$MI(Y, A_{n+1} | A_1 = a_1, \ldots, A_n = a_n) = \int_{A_{n+1}} \sum_y p(a_{n+1}, y | a_1, \ldots, a_n)$$

$$\log_2 \left( \frac{p(a_{n+1}, y | a_1, \ldots, a_n)}{p(a_{n+1} | a_1, \ldots, a_n) p(y | a_1, \ldots, a_n)} \right) da_{n+1};$$

in which $a_1, a_2, \ldots, a_n$ are the at least one first test results; Y is the question; y indicate possible results to the question; and $a_{n+1}$ are possible results for the second test considering additional factors using the information gain to obtain enhanced gain; responsive to the enhanced gain being below a threshold, continuing assessment with the first test result; and responsive to the enhanced gain being above or equal to the threshold: receiving test result for the second test; and continuing assessment with the first test result and second test result.

Yet another aspect of the disclosure relates to an apparatus having a processing unit and a storage device, the apparatus comprising: a result receiving component for receiving a result of a first test associated with a patient or a second test associated with a patient, and a question associated with a patient; an information gain determination component for assessing information gain provided by the second test which may be performed for the patient, as the conditional mutual information between the second test and the question, using the first test result.

Yet another aspect of the disclosure relates to a computer program product comprising: a non-transitory computer readable medium; a first program instruction for receiving a first test result and a question, both associated with a patient; and a second program instruction for assessing information gain provided by a second test which may be performed for the patient, as the conditional mutual information between a second test and the question, using the first test result, wherein said first, second, third and fourth program instructions are stored on said non-transitory computer readable medium.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
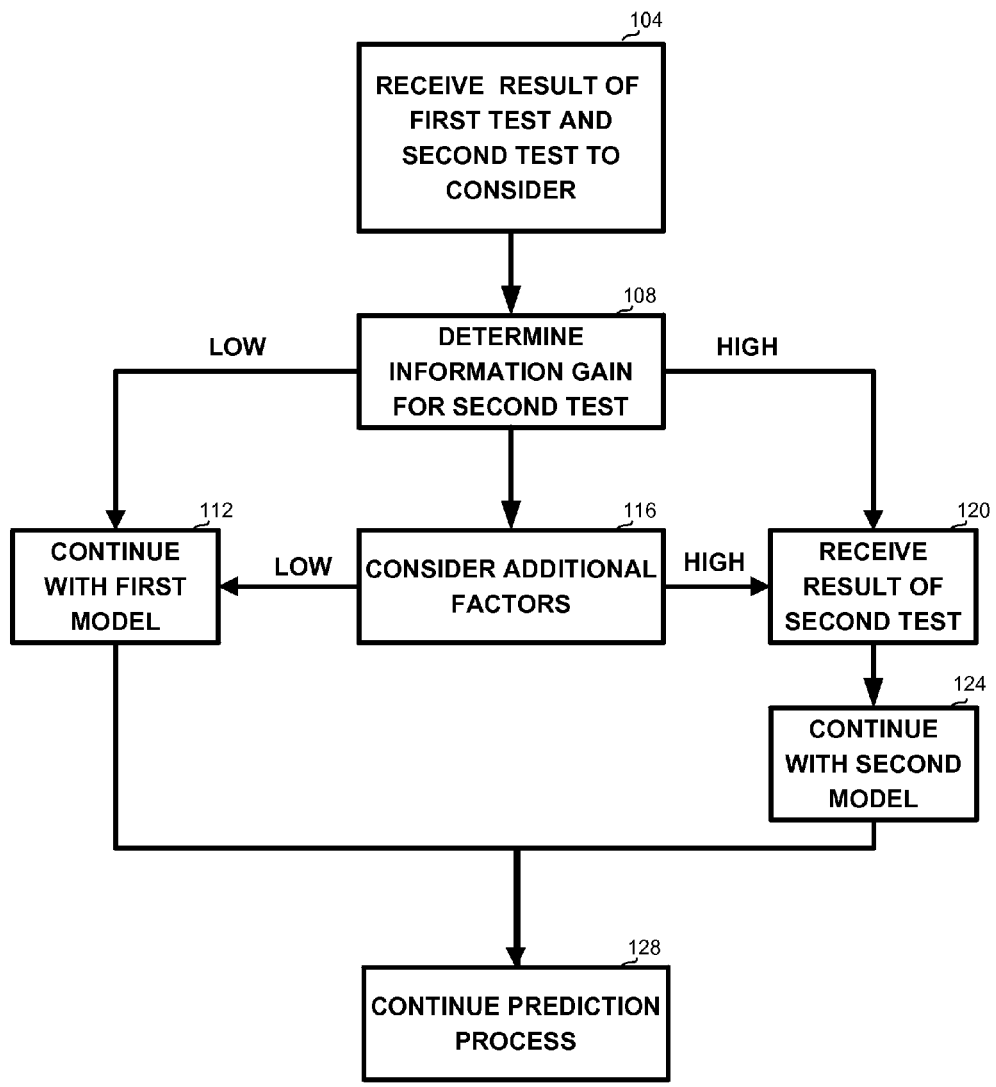
FIG. 1 shows a flow chart of steps in a method for assessing a state of a patient, in accordance with some exemplary embodiments of the disclosed subject matter.

The disclosed subject matter is described below with reference to flowchart illustrations and/or block diagrams of methods, apparatus (systems) and computer program products according to embodiments of the subject matter. It will be understood that blocks of the flowchart illustrations and/or block diagrams, and combinations of blocks in the flowchart illustrations and/or block diagrams, can be implemented by computer program instructions. These computer program instructions may be provided to one or more processors of a general purpose computer, special purpose computer, a processor, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transient computer-readable medium that can direct a computer or other programmable data processing apparatus to function in a particular manner, such that the instructions stored in the non-transient computer-readable medium produce an article of manufacture including instruction means which implement the function/act specified in the flowchart and/or block diagram block or blocks.

The computer program instructions may also be loaded onto a device. A computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

One technical problem dealt with by the disclosed subject matter is the need to take decisions in sequential testing environments, based on data such as demographic data or available test results. In such environments, tests are generally performed sequentially, and the decision whether to perform an additional test depends on its expected contribution vs. the associated risks, given existing test results. In many cases performing an additional examination clearly provides valuable information and improves the predictive model. However, there are cases in which the improvement is not constant for all values of previous tests, and quantification of possible improvement can support decision on whether or not to perform further examinations. In practice, at assessment time, the patient, the physician or the medical organization may decide to perform the additional test only if the expected improvement in prediction is cost worthy, thus preventing unworthy examinations while controlling possible decrease in prediction power. These considerations are particularly valuable when the additional tests require invasive or risky procedures or when there are financial limitations and patients or tests must be prioritized. In some cases, avoiding complicated unnecessary lengthy examinations can provide for earlier assessment at the point of care, or it may decrease the probability of false positive results and further unnecessary examinations and treatment.

Thus, the decisions about performing additional tests should be made based on their necessity, price and other information associated with the patient or the environment. The decision should be personalized for the patient and the patient state, the patient's preferences, and the circumstances, and should be taken dynamically.

One technical solution comprises the assessment of the information gain from performing an additional test given an existing set of test results.

Assuming the existence of n+1 tests denoted by $A_1 \ldots A_n$, $A_{n+1}$ and a future possible outcome or question denoted by Y, wherein values of tests $A_1 \ldots A_n$ are known, for example result $a_1$ for test $A_1$, result $a_2$ for test $A_2$, etc., it is required to decide whether to perform test $A_{n+1}$.

A conditional information gain, cInfoGain, may be defined as a measure that quantifies the possible additional information. In some embodiments, the cInfoGain of $a_1, a_2, \ldots, a_n$ may be defined as the conditional mutual information (MI) between biomarkers or possible results for test $A_{n+1}$ and Y given the values of the previous biomarkers. Calculating MI may require the estimation of the joint probability of tests or available biomarkers $A_1, \ldots, A_n, A_{n+1}$ and Y. However, joint distributions may be difficult to estimate, especially when the data set is relatively small Therefore, these distributions can be estimated using a parametric model, and the cInfoGain can be computed using numerical integration as follows:

$$cInfoGain(Y, A_{n+1} \mid A_1 = a_1, \ldots, A_n = a_n) = \qquad \text{Formula (1)}$$
$$MI(Y, A_{n+1} \mid A_1 = a_1, \ldots, A_n = a_n) =$$
$$\int_{A_{n+1}} \sum_y p(a_{n+1}, y \mid a_1, \ldots, a_n)$$
$$\log_2 \left( \frac{p(a_{n+1}, y \mid a_1, \ldots, a_n)}{p(a_{n+1} \mid a_1, \ldots, a_n) p(y \mid a_1, \ldots, a_n)} \right) da_{n+1}$$

The integral is over the various possible values of $A_{n+1}$, i.e., over the entire result set for test $A_{n+1}$, and the summation is over all possible answers to the question. For example, if the question is whether a person has diabetes or not, and $A_{n+1}$ is a blood test for a level of a certain marker such as a hormone, then the integral sums over the possible levels of the marker, and the summation would be over the possible answers to the question: the person has diabetes and the person does not have diabetes.

Thus cInfoGain is calculated as the sum over all answers and all results of the following: the conditional probability of the specific result and the specific answer given the available results, multiplied by the logarithm of the ratio between the same probability and the product of the conditional probability of the result given the available results and the conditional probability of the specific answer given the available results.

One technical effect of the disclosed subject matter may relate to evaluating the information gain provided by performing an additional test for assessing the state of a patient, when results of previous tests are available.

Another technical effect relates to usage of the information gain for a multiplicity of purposes. For example, the test may be performed only if the information gain exceeds a threshold which may be set by the caregiver, by the medical institute, or the like.

In other embodiments, given limited capacity for performing the additional test due for example to limited equipment availability or limited financial funds, the test may be performed for patients in decreasing order of the gained information, i.e., precedence will be given to those cases in which the additional test provides more information.

In yet other embodiments, when it is required to select which additional test to perform for a patient in order to assess the patient's state, the test that provides the highest information gain may be selected. Alternatively, the information gain may be weighted with additional considerations such as availability of the test, cost of the test, time until the test result is received, personal preferences of the patient or the caregiver, or the like.

Referring now to FIG. 1, showing a flowchart of steps in a method for assessing a state of a patient.

On step 104, results of one or more tests already performed for the patient may be received, together with a "question" such as a hypothesis, a possible diagnostics, or the like. The results and question may be received from an automated system, fed by a human operator, read from a file or a stream, or the like.

On step 108, the information gain for a second test may be determined. For example, the first test results may refer to a simple non-risky examination such as a blood test measuring the glucose level of a patient, while the second test may involve a radiology scan which is risky and expensive.

The information gain may be determined, using for example formula (1) disclosed above, which makes use of determining joint distributions:

$$cInfoGain(Y, A_{n+1} | A_1 = a_1, \ldots, A_n = a_n) =$$

$$MI(Y, A_{n+1} | A_1 = a_1, \ldots, A_n = a_n) = \int_{A_{n+1}} \sum_y p(a_{n+1}, y | a_1, \ldots, a_n)$$

$$\log_2 \left( \frac{p(a_{n+1}, y | a_1, \ldots, a_n)}{p(a_{n+1} | a_1, \ldots, a_n) p(y | a_1, \ldots, a_n)} \right) da_{n+1}$$

It will be appreciated that the information gain measure may be low for a set of one or more first test results in which there is little uncertainty about the prediction, i.e., there is high certainty about the existence or non-existence of the state, and for available results in which the assessment is not highly dependent on the second result, for example when the possible answers are substantially uniformly spread for the possible results of the second test. In such cases the second test does not contribute significant information beyond the first one, and the additional examination can be prevented.

If the information gain determined on step 108 is low, for example below a predetermined threshold, execution may continue at step 112, relating to continuing with a first model, for example providing prediction with only the available results.

If the information gain determined on step 108 is high, for example exceeds a predetermined threshold, execution may continue at step 120, relating to continuing with a second testing model which uses results of the second test.

In some embodiments, the information gain determined on step 108 may not be sufficient to take a decision, and execution may continue at step 116, in which additional factors may be considered to obtain enhanced gain. For example, any one or more of the following characteristics may be considered: patient or caregiver preferences, risks associated with the second test, alternative tests to be selected, financial considerations, limited resources for the second test, or the like.

For example, considering the additional factors may relate to determining to perform the second test if the information gain exceeds a threshold, comparing the information gain of the same test in respect to two patients and determining to perform the test for the person for whom the information gain is higher, comparing the information gain of the same patient in respect to two tests and determining to perform the test for which the information gain is higher, or the like.

If the enhanced gain obtained by considering the additional factors performed on step 116 is low or lower than another result, meaning that the combined considerations suggest not to perform the second test, execution may continue at step 112, relating to continuing assessment of the patient state with a first testing model which does not use results of the second test.

If, however, the enhanced gain is high, meaning that the combined considerations suggest performing the second test, the second test may be performed.

On step 120, the results of the second test may be received in any automated or manual manner.

On step 124, assessment of the patient state may continue with all available results, including those of the second test.

On step 128, the prediction process may continue for example by providing diagnostics or suggesting treatment, performing additional tests or repeating the steps above for an additional test, or the like.

In some embodiments, step 128, may be omitted and performed as part of steps 112 or 124 described above.

Figure 2:
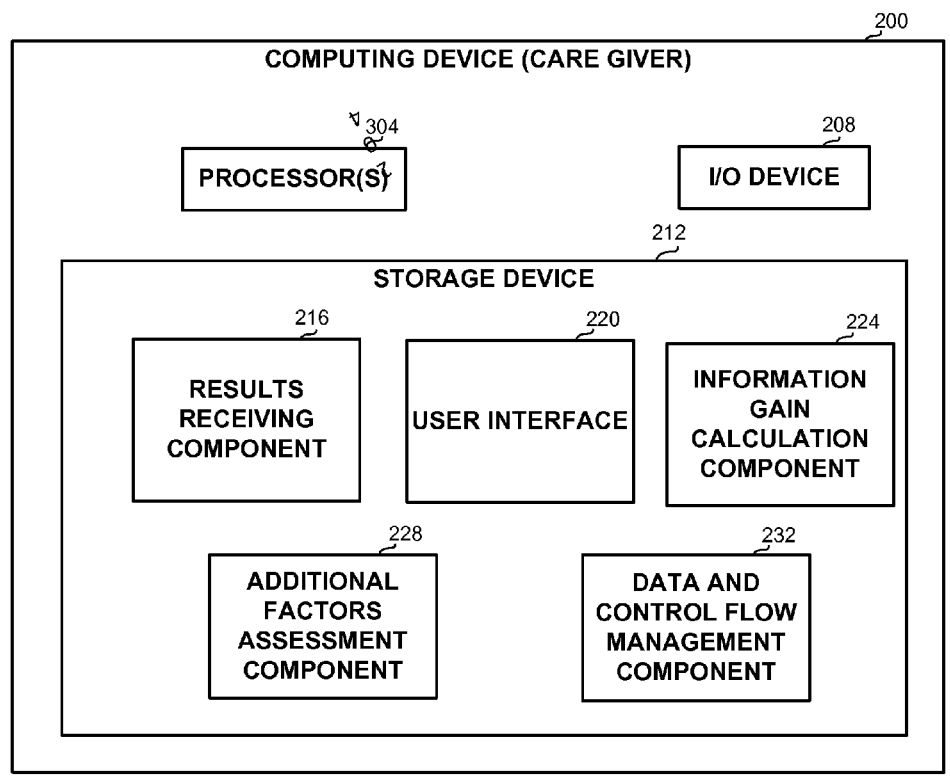
FIG. 2 shows a block diagram of components of an apparatus for assessing a state of a patient, in accordance with some exemplary embodiments of the disclosed subject matter.

Referring now to FIG. 2 showing a block diagram of components of an apparatus for clinical decision support.

The environment comprises a computing device 200, associated with a health organization having a multiplicity of data records related to patients having a disease. Computing device 200 may comprise one or more processors 204. Any of processors 204 may be a Central Processing Unit (CPU), a microprocessor, an electronic circuit, an Integrated Circuit (IC) or the like. Alternatively, computing device 200 can be implemented as firmware written for or ported to a specific processor such as digital signal processor (DSP) or microcontrollers, or can be implemented as hardware or configurable hardware such as field programmable gate array (FPGA) or application specific integrated circuit (ASIC). Processors 204 may be utilized to perform computations required by computing device 200 or any of it subcomponents.

In some embodiments, computing device 200 may comprise an input-output (I/O) device 208 such as a terminal, a display, a keyboard, an input device or the like to interact with the system, to invoke the system and to receive results. It will however be appreciated that the system can operate without human operation and without I/O device 208.

Computing device 200 may comprise one or more storage devices 212 for storing executable components, and which may also contain data during execution of one or more components. Storage device 212 may be persistent or volatile. For example, storage device 212 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, storage device 212 may retain program code operative to cause any of processors 204 to perform acts associated with any of the steps shown in FIG. 1 above, for example classifying data.

Storage device 212 may comprise or be in communication with one or more additional storage areas for storing patient data, test results or other data associated with the apparatus.

The components detailed below may be implemented as one or more sets of interrelated computer instructions, loaded to storage device 212 and executed for example by any of processors 204 or by another processor. The components may be arranged as one or more executable files, dynamic libraries, static libraries, methods, functions, services, or the like, programmed in any programming language and under any computing environment.

Storage device 212 may comprise or be loaded with results receiving component 216, which may receive results performed for a patient, in any manner, for example through communication with another computing platform, from a person using any of I/O devices 208 and a corresponding user interface component 220, or the like.

Storage device 212, may also comprise or be loaded with information gain calculation component 224 for determining the information gain provided by a test given a known set of test results, for example using formula (1) disclosed above. In Some embodiments, information gain calculation component 224 may comprise or may otherwise call joint distribution determination component 226 for determining the joint distribution, based on parametric model, real data or others.

Storage device 212 may also comprise or be loaded with additional factors assessment component 228 for assessing additional factors associated with the contribution of a test, such as alternative tests, resources, other patient's state or the like.

Additional factors assessment component 228 may, for example, determine to perform the second test if the information gain exceeds a threshold, compare the information gain of the same test in respect to two patients and determine to perform the test for the person for whom the information gain is higher, or compare the information gain of the same patient in respect to two tests and determine to perform the test for which the information gain is higher, or the like.

Storage device 212 may also comprise data and control flow management component 232 for managing the flow of the process, activating other components and providing the required data, or the like.

The disclosed apparatus can also be used by a patient assessing tests, in which the patient's preferences may be added to the considerations. The apparatus may also be implemented as a client-server system, in which each caregiver or user may access the capabilities of a server system while using a client system executed by another computing platform such as a laptop computer, a desktop computer, a mobile device, or the like. Some of the data, for example data associated with the tests may be provided from a shared location, while personal data may be provided from a more restricted storage.

Storage device 212 may also comprise data and statistics storage area 236 for storing calculation results, such as joint distributions, information gain results, or the like.

The disclosed method and apparatus may provide for assessing the risks and benefits associated with performing an additional test, given available results of some tests. Using an information-based measure, a considerable number of examinations can be avoided, while maintaining high predictive power of the used assessment model. The method may be used for quantifying the combination of the cost of the test with the possible predictive contribution of the test.

It will be appreciated that the method and apparatus may be applied to a given subset of two or more examinations, and to choosing a preferred test order for a patient.

It will be appreciated that some of the available tests may refer to demographic or other easy to gather information, and are not limited to medical procedures. Thus, the method and apparatus may be used even at preliminary assessment stages.

It will also be appreciated that the disclosed method and apparatus may be used for other purposes such as diagnostics or machines, and are not limited to the medical field.

The flowchart and block diagrams in the figures illustrate the architecture, functionality, and operation of possible implementations of systems, methods and computer program products according to various embodiments of the present disclosure. In this regard, each block in the flowchart and some of the blocks in the block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, any non-transitory computer-readable medium, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A computer-implemented method performed by a computerized device,
   receiving at least one first test result and a question, both associated with a patient; and
   assessing by a processor associated with a computing platform, information gain provided by a second test which may be performed for the patient, as the conditional mutual information between a second test and the question, using the at least one first test result;
   wherein the information gain is assessed using the formula of:

$$cInfoGain(Y, A_{n+1} | A_1 = a_1, \ldots, A_n = a_n) =$$
$$MI(Y, A_{n+1} | A_1 = a_1, \ldots, A_n = a_n) = \int_{A_{n+1}} \sum_y p(a_{n+1}, y | a_1, \ldots, a_n)$$
$$\log_2 \left( \frac{p(a_{n+1}, y | a_1, \ldots, a_n)}{p(a_{n+1} | a_1, \ldots, a_n) p(y | a_1, \ldots, a_n)} \right) da_{n+1};$$

wherein $a_1, a_2, \ldots, a_n$ are the at least one first test results; Y is the question; y indicates possible results to the question; MI is the conditional mutual information and $a_{n+1}$ are possible results for the second test.

2. The computer-implemented method of claim 1, further comprising considering one or more additional factors using the information gain.

3. The computer-implemented method of claim 2, wherein at least one of the one ore more additional factors is selected from the group consisting of: patient or caregiver preferences; a risk associated with the second test; alternative test to the second test; a financial consideration; and a limited resource for the second test.

4. The computer-implemented method of claim 2, wherein considering the one ore more additional factors comprises determining to perform the second test, responsive to the information gain exceeding a predetermined threshold.

5. The computer-implemented method of claim 4, further comprising performing the second test.

6. The computer-implemented method of claim 2 wherein considering the one or more additional factors comprises: performing said receiving and said assessing for at least two patients and determining to perform the second test for one of the at least two patients having higher information gain; or performing said receiving and said assessing for at least a pair of second tests and determining to perform one of the at least the pair of second test for which the information gain is higher.

7. A computer-implemented method performed by a computerized device, comprising:
   receiving a first test result and a question, both associated with a patient;
   assessing the information gain provided by a second test to be performed for the patient as the conditional mutual information between a second test and the question, using the first test result, in accordance with the formula of:

$$cInfoGain(Y, A_{n+1} | A_1 = a_1, \ldots, A_n = a_n) =$$
$$MI(Y, A_{n+1} | A_1 = a_1, \ldots, A_n = a_n) = \int_{A_{n+1}} \sum_y p(a_{n+1}, y | a_1, \ldots, a_n)$$
$$\log_2 \left( \frac{p(a_{n+1}, y | a_1, \ldots, a_n)}{p(a_{n+1} | a_1, \ldots, a_n) p(y | a_1, \ldots, a_n)} \right) da_{n+1};$$

in which $a_1, a_2, \ldots, a_n$ are the at least one first test results; Y is the question; y indicate possible results to the question; MI is the conditional mutual information; and $a_{n+1}$ are possible results for the second test considering additional factors using the information gain to obtain enhanced gain;
   responsive to the enhanced gain being below a threshold, continuing assessment with the first test result; and
   responsive to the enhanced gain being above or equal to the threshold:
     receiving test result for the second test; and
     continuing assessment with the first test result and second test result.

8. The computer-implemented method of claim 7, further comprising performing the second test.

9. An apparatus having a processing unit and a storage device, the apparatus comprising:
   a result receiving component for receiving a result of a first test associated with a patient or a second test associated with a patient, and a question associated with a patient;
   an information gain determination component for assessing information gain provided by the second test which may be performed for the patient, as the conditional mutual information between the second test and the question, using the first test result, wherein the information gain determination component is adapted to assess the information gain using the formula of:

$$cInfoGain(Y, A_{n+1} | A_1 = a_1, \ldots, A_n = a_n) =$$

$$MI(Y, A_{n+1} | A_1 = a_1, \ldots, A_n = a_n) = \int_{A_{n+1}} \sum_y p(a_{n+1}, y | a_1, \ldots, a_n)$$

$$\log_2\left(\frac{p(a_{n+1}, y | a_1, \ldots, a_n)}{p(a_{n+1} | a_1, \ldots, a_n) p(y | a_1, \ldots, a_n)}\right) da_{n+1}$$

Wherein $a_1, a_2, \ldots, a_n$ are the at least one first test results; Y is the question; y indicated possible results to the question; MI is the conditional mutual informationl and $a_{n+1}$ are possible results for the second test.

10. The apparatus of claim 9, further comprising an additional factors assessment component for considering one or more additional factors using the information gain.

11. The apparatus of claim 10 wherein at least one of the one or more additional factors is selected from the group consisting of: patient or caregiver preferences; a risk associated with the second test; alternative tests to the test; a financial consideration; and a limited resource for the second test.

12. The apparatus of claim 10 wherein the additional factors assessment is adapted for determining to perform the second test responsive to the information gain exceeding a predetermined threshold.

13. The apparatus of claim 10 wherein the additional factors assessment is adapted for performing an action selected from the group consisting of: performing said receiving and said assessing for at least two patients and determining to perform the second test for one of the at least two patients having higher information gain; and performing said receiving and said assessing for at least a pair of second tests for one patient and determining to perform one of the at least the pair of second tests for which the information gain is higher.

14. The apparatus of claim 9, further comprising a joint distribution determination component for determining joint distribution of events.

15. An apparatus having a processing unit and a storage device, the apparatus comprising:
- a result receiving component for receiving a result of a first test associated with a patient or a second test associated with a patient, and a question associated with a patient;
- an information gain determination component for assessing information gain provided by the second test which may be performed for the patient, as the conditional mutual information between the second test and the question, using the first test result; and
- a data ad statistics storage area for storing calculation results.

* * * * *